US00PP34074P3

(12) United States Plant Patent
Bodapati et al.

(10) Patent No.: US PP34,074 P3
(45) Date of Patent: Mar. 29, 2022

(54) *PONGAMIA* TREE NAMED 'K207'

(50) Latin Name: ***Pongamia pinnala* (L) Pierre**
Varietal Denomination: K207

(71) Applicant: TerViva, Inc., Oakland, CA (US)

(72) Inventors: Naidu Bodapati, Riverhills (AU); Marshall MacKay, Tewantin (AU); Naveen Sikka, Oakland, CA (US); David Harry, Philomath, OR (US)

(73) Assignee: Terviva, Inc., Oakland, CA (US)

( * ) Notice: Subject to any disclaimer, the term of this patent is extended or adjusted under 35 U.S.C. 154(b) by 0 days.

(21) Appl. No.: 16/602,152

(22) Filed: Aug. 14, 2019

(65) Prior Publication Data

US 2020/0068765 P1 Feb. 27, 2020

Related U.S. Application Data

(60) Provisional application No. 62/722,102, filed on Aug. 23, 2018.

(51) Int. Cl.
*A01H 5/00* (2018.01)
*A01H 6/54* (2018.01)

(52) U.S. Cl.
USPC ..... Plt./216
CPC ..... *A01H 6/54* (2018.05)

(58) Field of Classification Search
USPC ..... Plt./216
CPC ..... A01H 6/54; A01H 5/00
See application file for complete search history.

(56) References Cited

U.S. PATENT DOCUMENTS

PP26,060 P3 11/2015 Bodapati et al.
PP26,061 P3 11/2015 Bodapati et al.
PP26,062 P3 11/2015 Bodapati et al.

OTHER PUBLICATIONS

Biswas et al. (Int. J. Mol. Sci. 15: 7380-7397, 2014).*
Statement of claim filed in the Supreme Court of Queensland by Bioenergy Plantations Australia Pty Ltd. dated Oct. 9, 2020, 15 pages.

* cited by examiner

*Primary Examiner* — Keith O. Robinson
(74) *Attorney, Agent, or Firm* — Morrison & Foerster LLP

(57) ABSTRACT

A new and distinct variety of *Pongamia* tree (*Pongamia pinnata* (L) Pierre) named 'K207' is provided herein. *Pongamia* tree 'K207' is distinguished by having a dense canopy, large leaves with dark yellowish green color, semi-pendulous branches, unusually large lenticels on the stems, compact inflorescences, abundant production of seed pods, coupled with the high oil content of the seeds.

11 Drawing Sheets

Latin name:

Botanical classification: *Pongamia pinnata* (L) Pierre.

Varietal denomination: The varietal denomination of the claimed variety of *Pongamia* tree is 'K207'.

BACKGROUND OF THE INVENTION

*Pongamia* is a species of tree that belongs to the Fabaceae family of plants. The botanical classification of *Pongamia* is *Pongamia pinnata* (L) Pierre, although these plants are also known by a number of synonymous botanical classifications including, for example, *Millettia pinnata* (L) Panigrahi, *Derris indica* (Lam.) Bennet, *Pongamia glabra* Vent, and *Cytisus pinnatus* (L).

As a member of the Fabaceae family of plants, *Pongamia* trees are legumes and are capable of fixing their own nitrogen. *Pongamia* can grow well in a variety of environmental conditions, including areas with malnourished soil. *Pongamia* seeds also contain a profile of chemicals having a number of uses including, for example, commercial preparation into skin ointment and as a fuel source.

*Pongamia* trees are capable of growing in otherwise challenging environmental conditions and produce seed oils with beneficial properties. There exists a need for *Pongamia* varieties that are stable, high yielding, and agronomically sound.

SUMMARY OF THE INVENTION

In order to meet these needs, the present disclosure is directed to an improved variety of *Pongamia* tree. In particular, the disclosure relates to a new and distinct variety of *Pongamia* tree (*Pongamia pinnata* (L) Pierre), which has been denominated as 'K207'.

*Pongamia* tree 'K207' was discovered growing in a cultivated area in southeastern Queensland, Australia, wherein it and neighboring trees are grown for shade and other landscape amenities. The parentage of this tree is unknown, as is typical for trees cultivated in landscape plantings of this type.

The original donor tree (and source of clonal material) of 'K207' was identified and selected primarily on the basis of its consistent production of large and abundant seed pods, coupled with the high oil content (40.6%, dry-weight basis) of its large seeds. This selected individual was assigned identity number 'K207'. Subsequently, branch cuttings were collected from the donor tree and rooted by treating the cuttings with the rooting hormone indolebutyric acid (IBA) using either an aqueous solution of IBA (500 ppm) or a commercially available rooting powder. Dehydration of the cuttings was avoided by placing them in moistened rooting medium within a humid enclosed chamber. Rooting success varies from one collection event to another, which is normal for cuttings from mature trees. Typically, 10% or more of the cuttings initiated root development within 3-4 weeks.

*Pongamia* tree 'K207' has been asexually reproduced via rooted cuttings in the Brisbane area of Queensland, Australia, as well as in Texas and Florida, U.S.A. In addition, shoots of 'K207' have also been grafted onto seedling rootstock using either a top-cleft graft or a side-veneer graft. These asexually propagated plants remain true-to-type, and show considerable resemblance among one another after accounting for variation in overall size of the propagated cuttings and seedling rootstocks.

*Pongamia* tree 'K207' is particularly and distinctly characterized by its very dense canopy, long current seasons semi-pendulous branchlets, unusually large oval to circular lenticels on stem, compact inflorescences, and bearing copious quantities of fruit pods containing seeds with high seed-oil content (40.6%, dry-weight basis). Pods tend to appear in dense clusters. 'K207' demonstrates excellent vigor, with casual observations suggesting it is reasonably resistant to insect and disease pests, at least relative to other *Pongamia* trees growing in the general vicinity. However, susceptibility or resistance to specific insect and disease pests has not been determined.

DESCRIPTION OF THE DRAWINGS

*Pongamia* tree 'K207' is illustrated by the accompanying photographs, which show e.g. the plant's form, branches, foliage, leaves, trunk, pods, and seeds as specifically described below. The colors shown are as true as can be reasonably obtained by conventional photographic procedures.

DETAILED BOTANICAL DESCRIPTION OF THE PLANT

Figure 1:
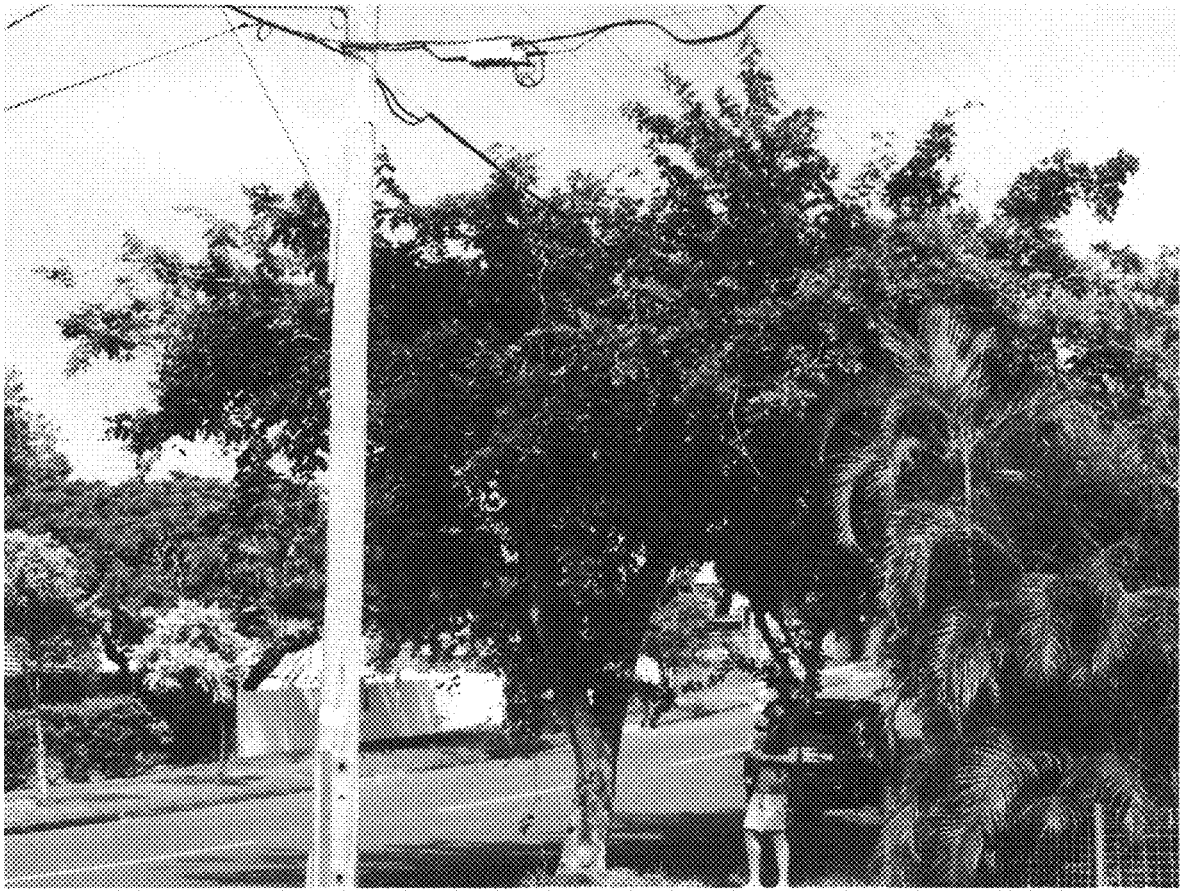
FIG. 1 illustrates a view of the whole tree of *Pongamia* tree 'K207' in Queensland, Australia. The depicted tree was estimated to be 15-20 years old when photographed.
Figure 2:
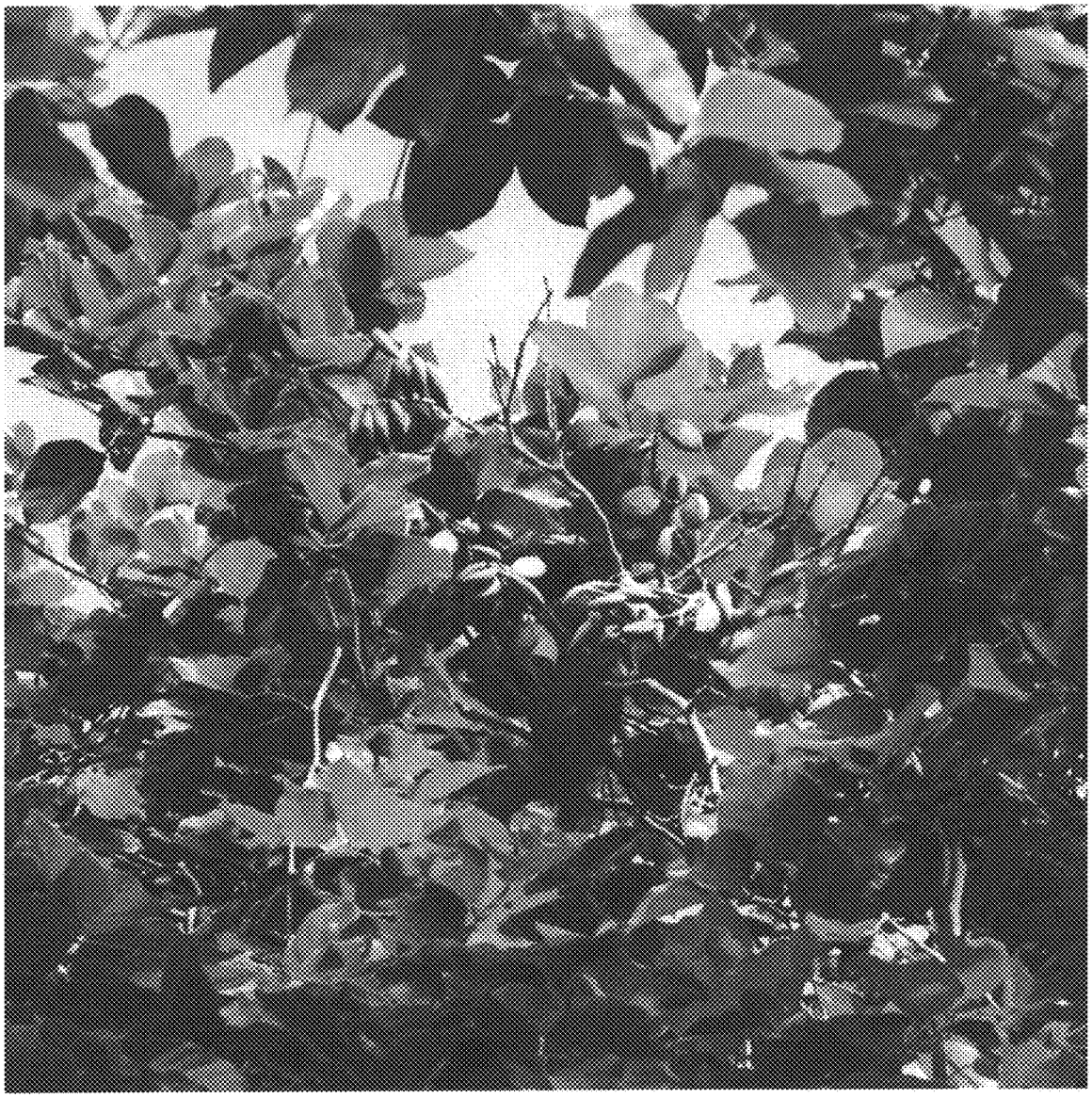
FIG. 2 illustrates a view of the leaves and seed pods on *Pongamia* tree 'K207' in Queensland, Australia. The depicted tree was estimated to be 15-20 years old when photographed.
Figure 3:
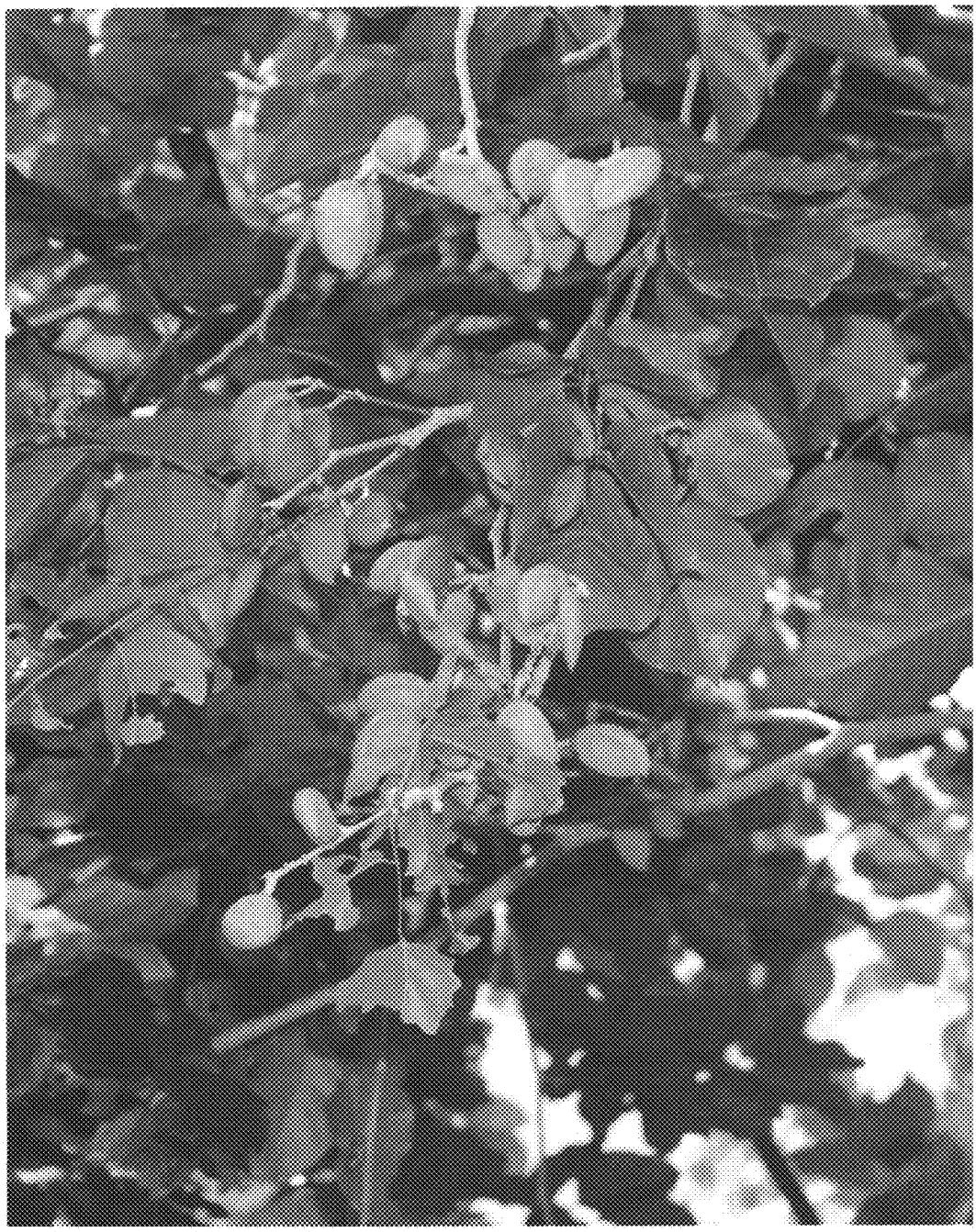
FIG. 3 illustrates a view of the leaves and seed pods on *Pongamia* tree 'K207' in Queensland, Australia. The depicted tree was estimated to be 15-20 years old when photographed.
Figure 4:
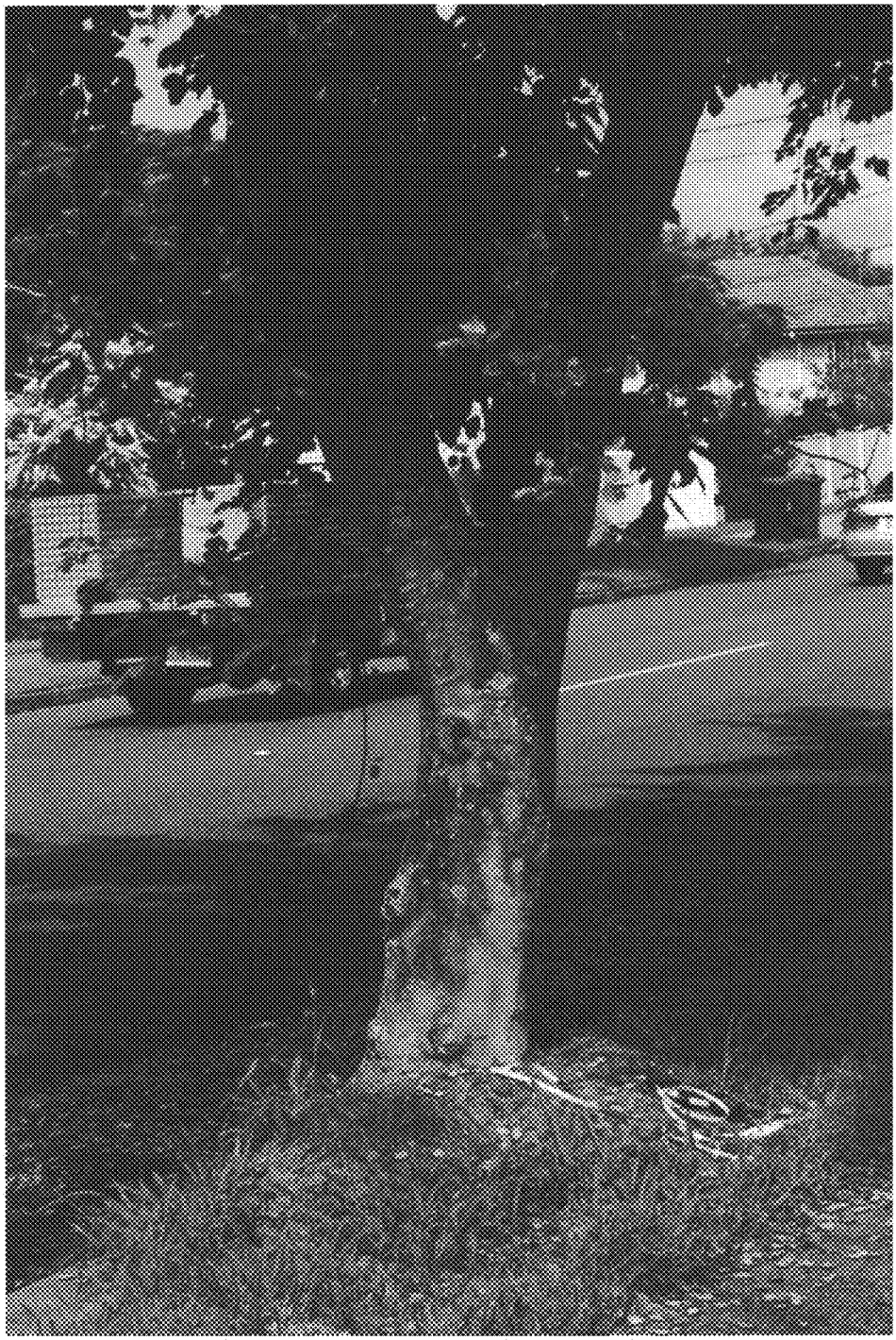
FIG. 4 illustrates a view of the tree trunk of *Pongamia* tree 'K207' in Queensland, Australia. The depicted tree was estimated to be 15-20 years old when photographed.
Figure 5:
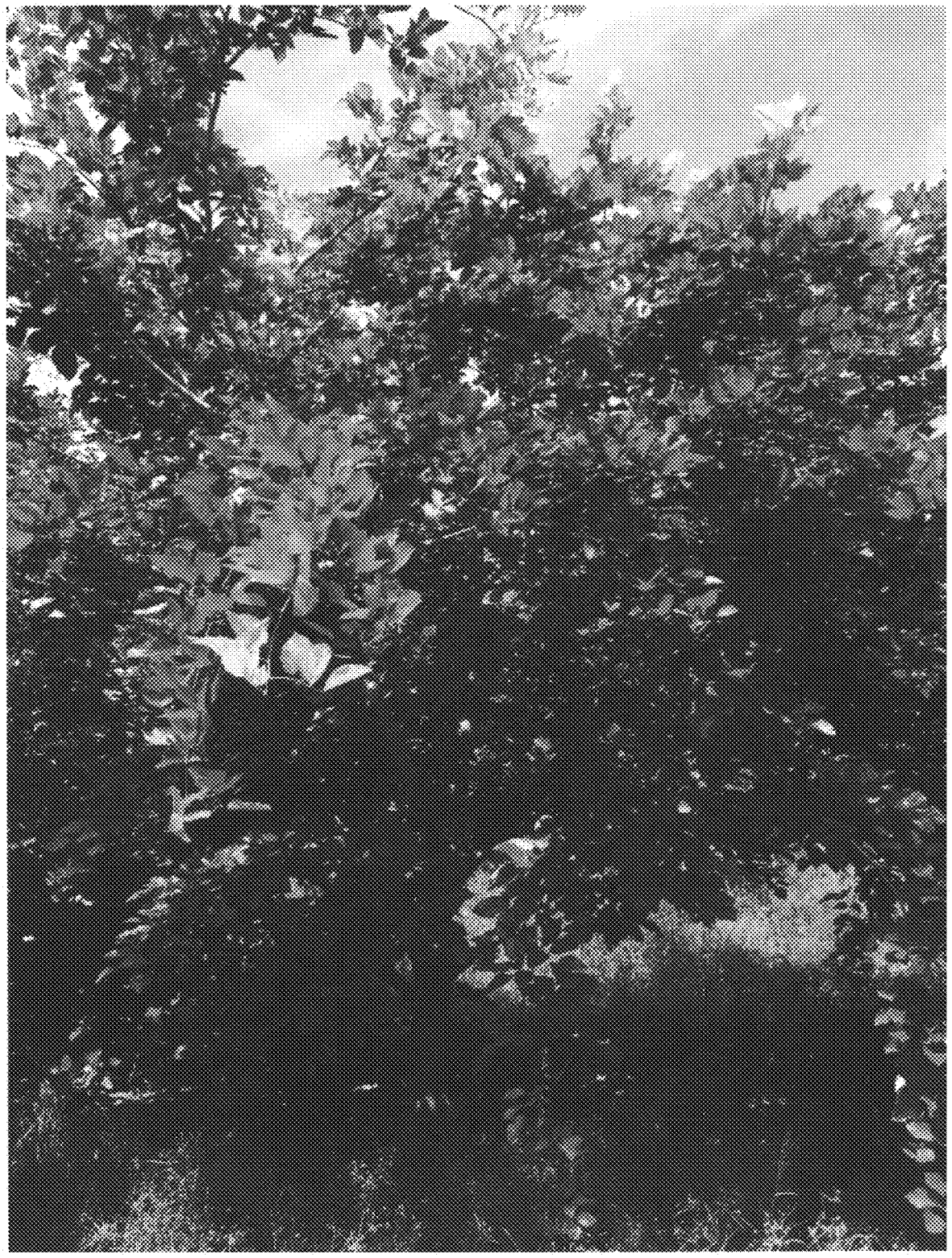
FIG. 5 illustrates a view of a 5-year-old clonally propagated 'K207' tree in Florida, USA.
Figure 6:
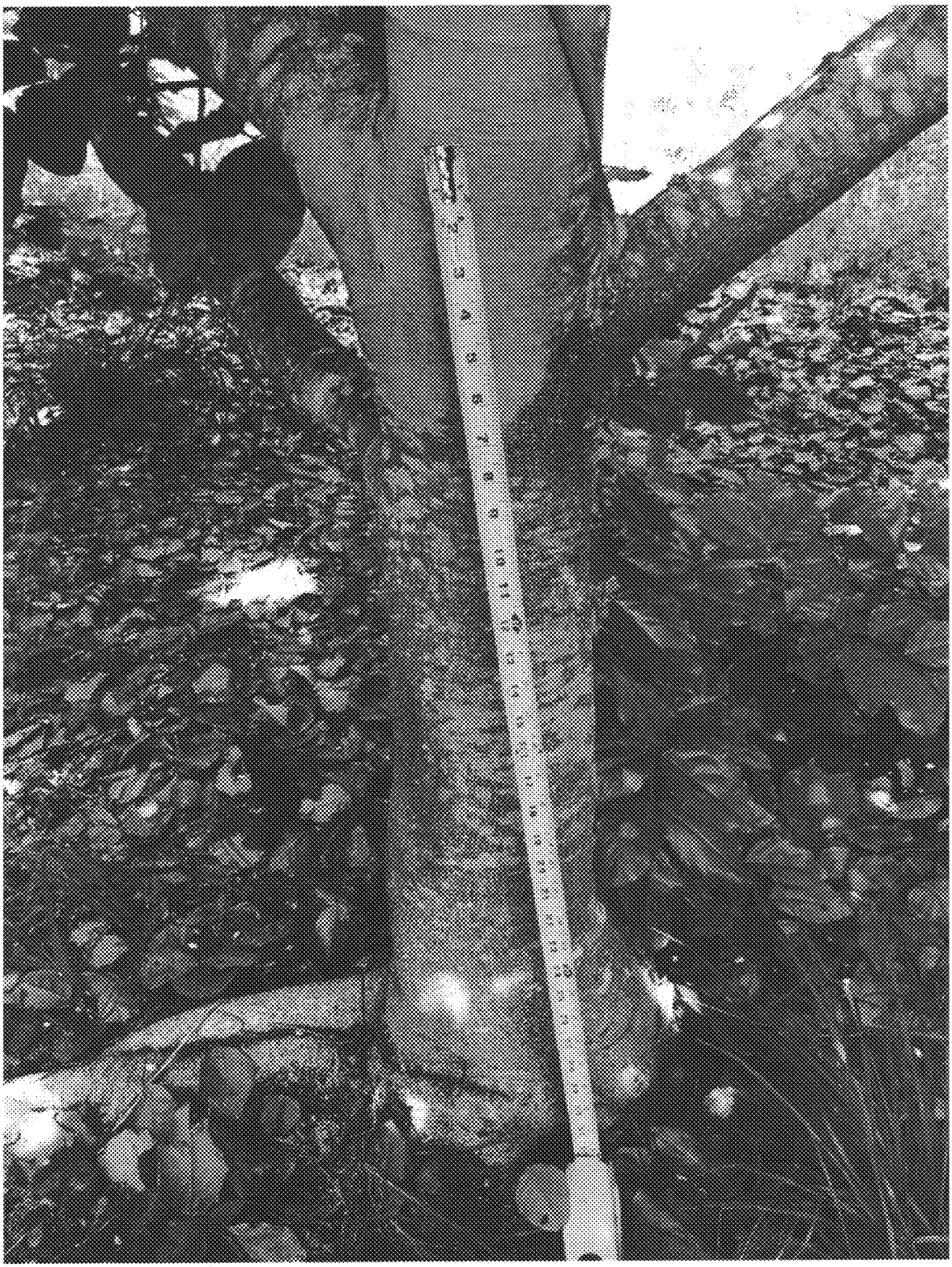
FIG. 6 illustrates a 5-year-old clonally propagated 'K207' tree in Florida with the smooth colored bark on the main trunk. Mottled patches on the bark primarily reflect differences in lichen growth. Unusually large stretched lenticular scars appear as horizontal striations along the bark.
Figure 7:
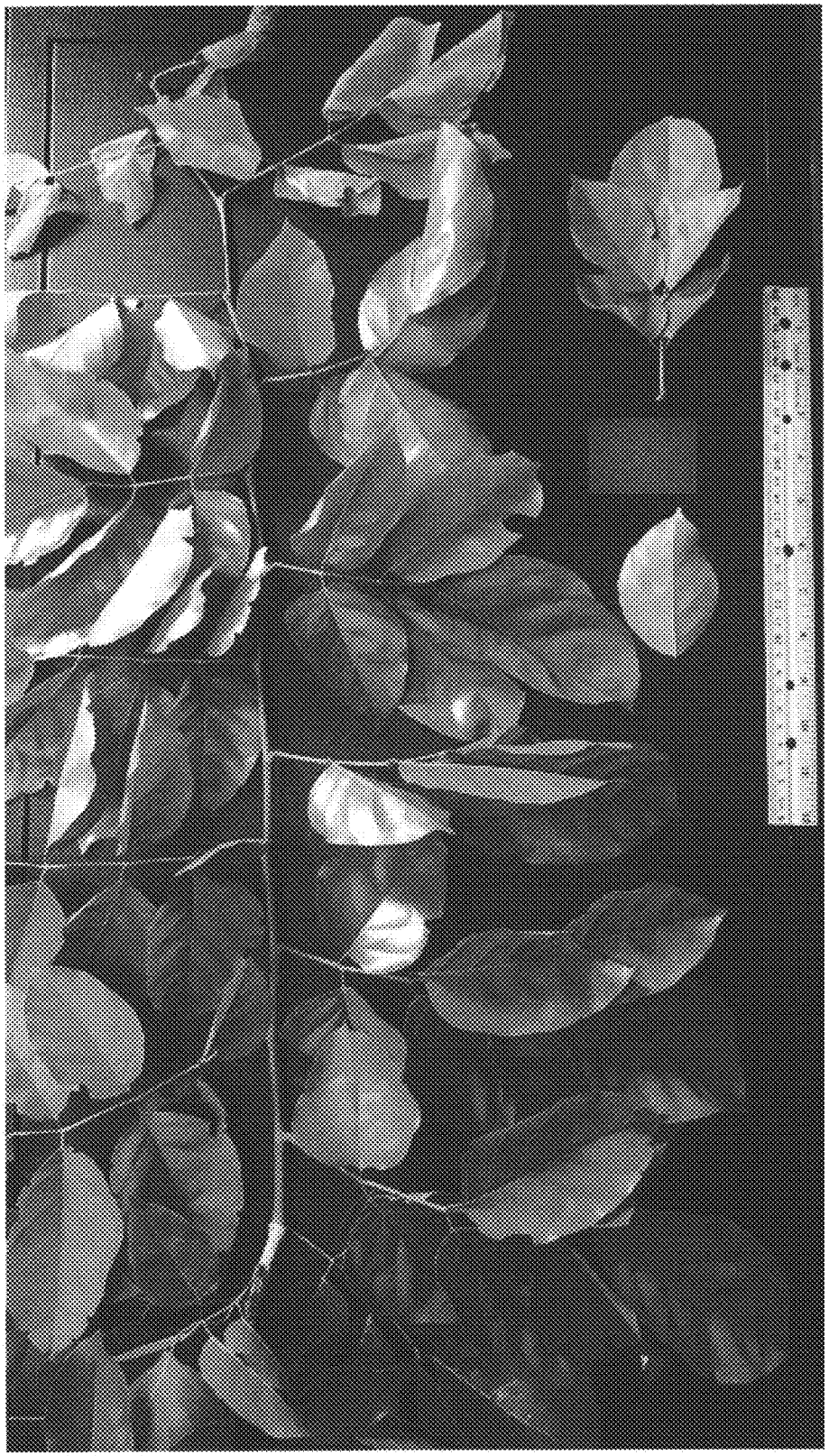
FIG. 7 illustrates the long current season's branch with odd-pinnately compound leaves from a 5-year-old clonally propagated 'K207' tree in Florida. The compound leaves typically bear a mix of leaves with either 5 (more common) or 7 leaflets. The leaf on the right is oriented to show the underside.
Figure 8:
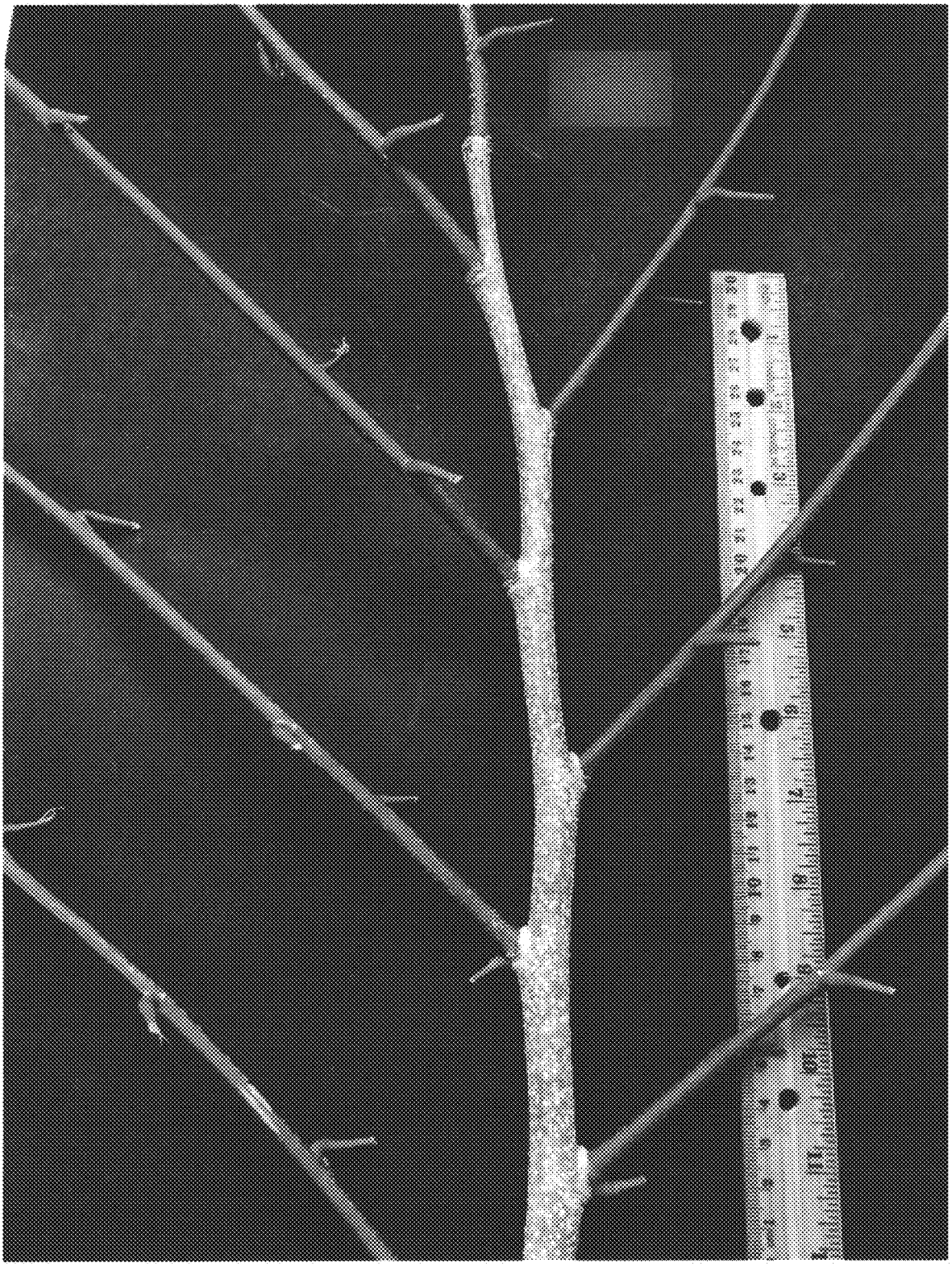
FIG. 8 illustrates the regular branching pattern arising from the leaf axils, and long current season's twigs on a 5-year-old clonally propagated 'K207' tree in Florida. Leaves have been removed for clarity.

The following detailed description sets forth the phenotypic characteristics and the distinctive features of *Pongamia* tree 'K207'. Descriptions are from trees that are 5 years post-transplant into the field in Florida, USA unless otherwise noted. Standardized color designations herein are with reference to The Royal Horticultural Society (R.H.S.) Mini Colour Chart, Sixth Edition, 2015.

Classification:

*Family*.—Fabaceae.

*Botanical*.—*Pongamia pinnata* (L) Pierre.

*Common name*.—Pongam tree, pongam oil tree, or *Pongamia*.

Tree:

*Size*.—Very vigorous tree of substantial size and stature, 8 m in height. Crown diameter, measured at the drip-line in two dimensions, is 6 m×6.5 m.

*Trunk*.—The trunk is bifurcated at a height of 55 cm from the ground, with the average breast-height diameter of these two major measuring 11 cm. The trunk can have numerous epicormic branches at its base (this trait is variable among trees). On 5-year-old trees in Florida, epicormic branches numbered 0-5 along the basal 61 cm of the main trunk, averaging 3. The fresh vegetative growth on an epicormic shoot ranges from 25 cm to 60 cm long and from about 4.0 mm to 7.5 mm in diameter.

*Bark*.—Greyish yellow green in color (RHS 196A) with smooth or faintly vertically fissured bark on the main trunk. Light-colored light greenish grey (RHS 190D) and dark-colored very pale green (RHS 192B) mottled patches on the bark reflect differences in lichen growth.

*Form*.—Decurrent crown with younger open-grown trees having greater breadth than height. Average height of five four-year-old trees in Florida was 3.5 m (range of 2.7 to 4.7 m) whereas their average crown width was 6.4 m (range of 5.8 to 7.0 m). The canopy is characterized by dense, compact foliage and the outer branchlets show semi-pendulous character.

Branches:

*Branch numbers and dimensions*.—Primary branches from the main stem are stout. On a 5-year-old tree in Florida, the average breast-height diameter of two major stems (bifurcated at 55 cm) is 11 cm. Height of primary branching often reflects management activities because a clear basal stem is preferred. In a second Florida field, with 4-year-old trees, 3 to 4 primary branches occurred at a height of 65-80 cm and averaged 7.9 cm in diameter (range 6.7-10.6 cm). The bark color of these branches closely resembles the color of the main trunk (greyish yellow green, RHS 196A). Each primary branch included 2-4 secondary branches, with basal diameters averaging 4.5 cm (range 3.8-5.6 cm).

*Branching habit*.—Many smaller branches occur on the periphery of the crown, but are too numerous to count. These peripheral branches result in a dense canopy that arises, in part, from the elongation of axillary buds to form axillary shoots along year-old shoots (i.e. wood from the previous year). Averaged over three branches on each of three trees, the outermost meter of year-old stem encompassed 20.2 nodes, three of which bore an axillary shoot.

*Buds and shoots*.—Young shoots emerge from naked lateral buds, with the most distal bud (a false terminal bud) giving rise to a new terminal shoot. Buds are hemispherical and range from 3.2 mm to 5.0 mm wide at their base. Buds protrude outward 2.0 mm to 3.0 mm from the stem and are between 1.5 mm to 2.0 mm thick. The typical axillary bud is strong yellow green in color (RHS 144A), and the younger terminal bud is also strong yellow green in color (RHS 144A).

*Terminal shoots*.—The seasonal elongation of terminal shoots is considerable. Total elongation growth of the terminal shoots is an average of 45 cm and encompassing an average of 7 internodes. The average stem diameter of terminal shoots is 20.0 mm.

*Lateral shoots*.—Seasonal elongation of lateral shoots is considerably long, with an average length of 55 cm and bearing 8 leaf nodes. The average diameter of lateral shoots is 5.3 mm.

Figure 9:
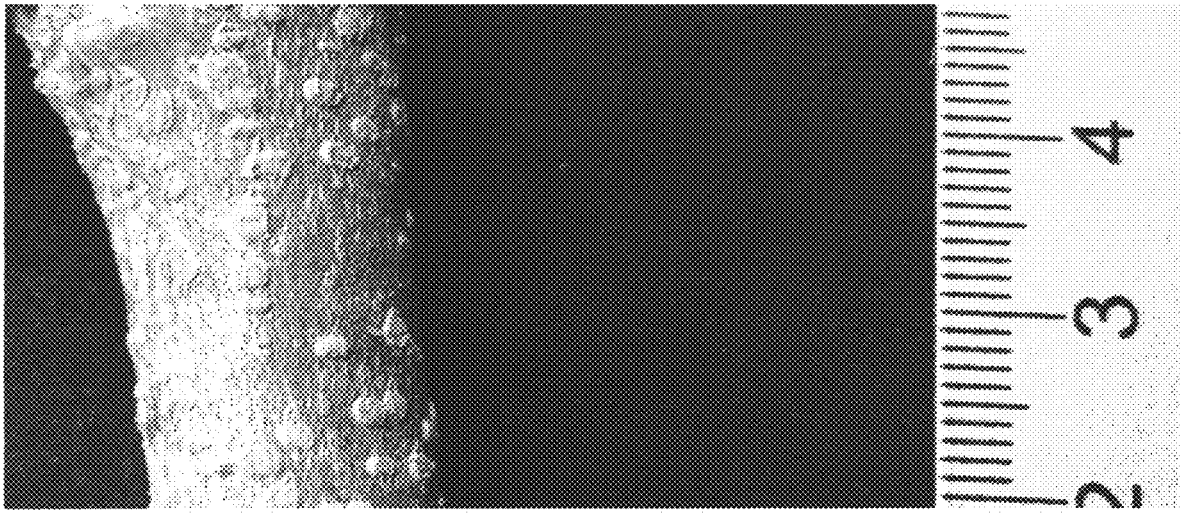
FIG. 9 illustrates the unusually large lenticels, especially on the previous season's wood, from a 5-year-old clonally propagated 'K207' tree in Florida.
Figure 10:
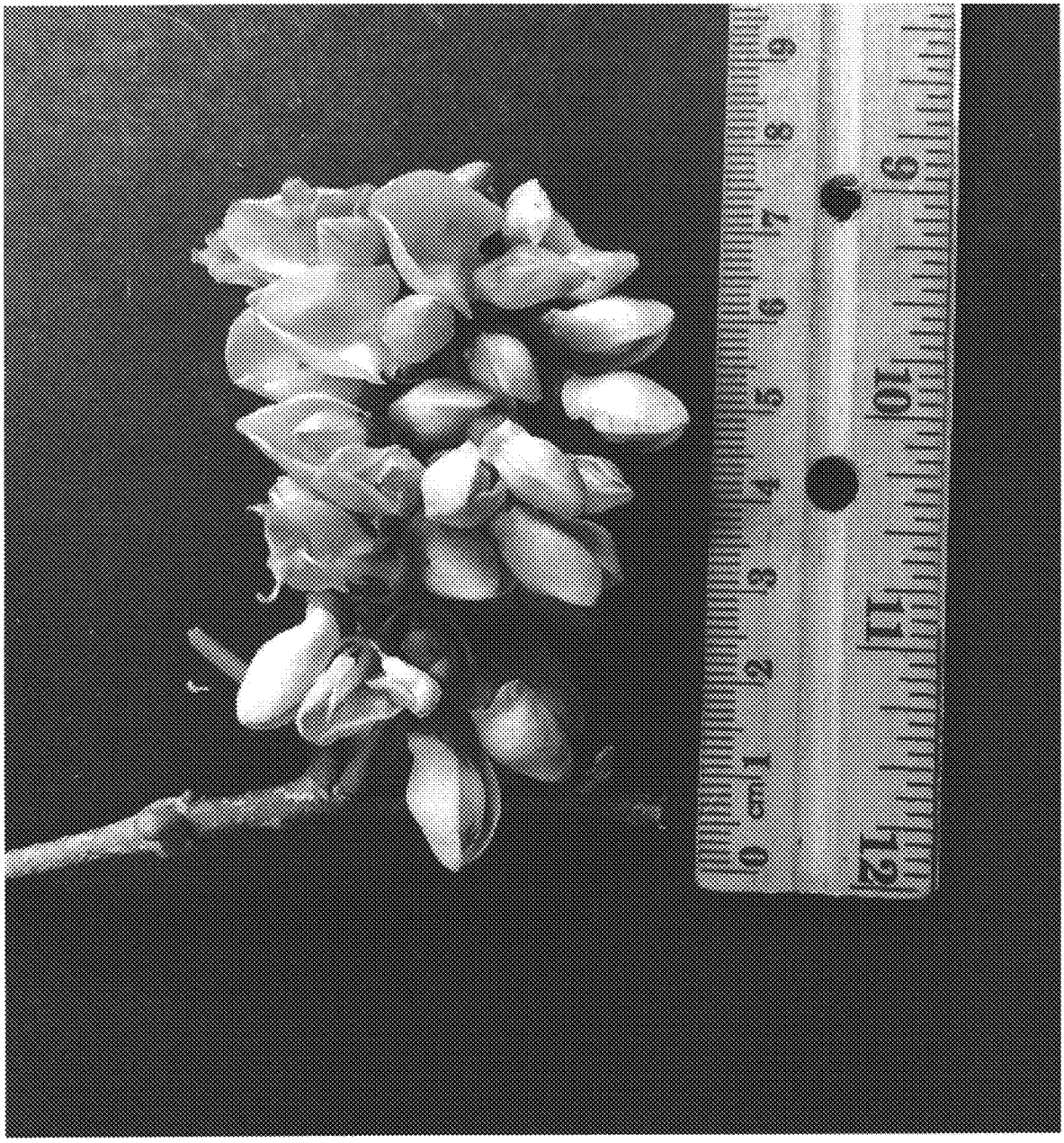
FIG. 10 illustrates the compact inflorescences from a 5-year-old clonally propagated 'K207' tree in Florida.
Figure 11:
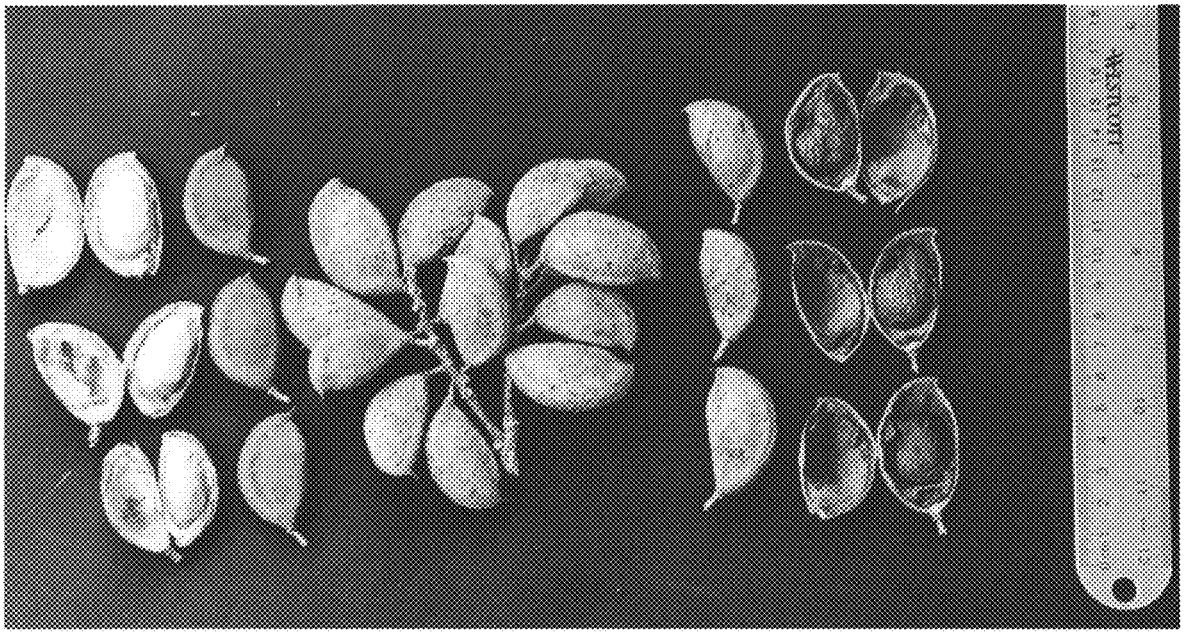
FIG. 11 illustrates semi-mature pods along with fully mature dry pods of *Pongamia* tree 'K207'. Both pod stages have been split open to show seed. The branch shown has 2 rachises borne in the axils of basal leaves. Each rachis bears 3-6 immature pods. Semi- and fully-mature pods are from a 5-year-old clonally propagated 'K207' tree in Florida.

*Shoot and twig surfaces*.—Woody twigs have leaf scars that are 5.0 mm to 6.0 mm wide, showing traces of three vascular bundles. The central scar tends to have a border that is less distinct than the outer two. Branchlets are hairless with yellowish white stipule scars (RHS 158C). The youngest shoots are distinctly strong yellow green in color (RHS 143A) and flexible, with no lenticels apparent to the naked eye. As shoots mature, their color shifts to pale yellow green (RHS 194D) and prominent lenticels become visible as raised, light yellow-colored (RHS 162C) corky circles. 'K207' as shown in FIG. 9 displays large oval to circular lenticels averaging 2.5 mm in diameter; a characteristic that contrasts with other similar *Pongamia* cultivars.

Leaves:

*General*.—Alternate, imparipinnate with long slender leafstalk, and hairless. About ⅔ (two-thirds) of leaves show 5 leaflets, and about ⅓ (one-third) of leaves shows 7 leaflets.

*Size and shape*.—The outline of a compound leaf is roughly oval to elliptic, with an average length of 30 cm and an average width of 16 cm.

*Leaflets*.—Blades of individual leaflets are ovate to cordate in shape with a cuspidate to mucronate apex. Leaflet venation tends to be arcuate. Blades of terminal leaflets have an average length of 12 cm and an average width of 8 cm. The smallest leaflet on a leaf tends to be a basal leaflet with an average length of 10 cm and an average width of 7 cm.

*Leaflet color, surface, and texture*.—Leaflets are glabrous on both abaxial and adaxial surfaces. Young leaves exhibit a strikingly glossy cuticle on their adaxial surface. The adaxial (upper) and abaxial (lower) surfaces of a younger leaflet are strong yellow green in color (RHS 144A for adaxial surface, and RHS 141A for abaxial surface). The adaxial surface of an older leaflet is moderate dark yellowish green in color (RHS 139A), and the abaxial surface of an older leaflet is moderate olive green in color (RHS 146A) with prominent veins beneath. The color changes described above accompany the gradual maturation of younger to older leaves (and leaflets), occurring over several (3-5) weeks, depending on the season. As they mature, leaves and leaflets also become increasingly sclerophyllous.

*Stipules*.—A pair of elliptical stipules subtends the youngest leaves on a shoot. Stipules are strong yellow green (RHS 144A) and are approximately 10 mm long by 3 mm wide, with a glabrous surface and entire margins. Stipules remain for only a short duration (1-2 weeks) before they dehisce.

Flowers and inflorescences:

*General*.—Hermaphroditic florets are borne on an indeterminate inflorescence.

*Inflorescence structure*.—Several florets are clustered into a fascicle node, which are generally evenly distributed along a rachis. The entire inflorescence is a pseudoraceme. Most inflorescences are unbranched, but some are branched.

*Position in crown*.—'K207' has compact inflorescences with an average length of 11 cm. There are an average of 3 inflorescences per lateral shoot. Inflorescences are borne in the basal leaf axils of the current year's vegetative flush, and near the distal end of the prior year's shoot growth. Each rachis may hold an average 80 florets.

*Florets*.—Emerge acropetally from a fused ovoid calyx with entire margins and glabrous texture. The calyx has an average depth of 4.0 mm and width of 4.5 mm, and is moderate brown in color (RHS 16A). The average length of pedicles is 7.0 mm and the average diameter is 0.5 mm. Pedicels can be dark purple (RHS 83A). Zygomorphic florets consist of 2 keel, 2 wing, and a standard (or banner) petal, and have a depth of 12.1 mm and a diameter of 10.5 mm. The banner petal has a tint of light purplish pink color (RHS 62C) towards the edges, and a strong yellow (RHS N144B) streak in the middle. The banner petal's apex does not have a split notch, and the base is rounded. Wing petals are typically 7.7 mm long and the exposed part is very light purple in color (RHS 75C). The two keel petals are fused together enclosing the stamens and pistil, it is white in color (RHS NN155D), and the distal edges display dark greyish yellow color (RHS 199D). The 10 stamens are fused and enclose the pistil.

*Flowering period*.—Relative to other *Pongamia* cultivars in the general area, 'K207' tends to flower about mid-range into the flowering period (from November to December in southeastern Queensland, Australia; and early June in Florida, USA).

Fruits:

*General*.—Only one of the two ovules develop into a seed in most of the pods. Immediately after fertilization, the peduncular ovule usually aborts and remains as a small unfilled seed. Only the stigmatic ovule develops into seed, thus pods usually bear a single seed.

*Shape and color*.—Developing fruits first appear as moderate yellow green (RHS 146C) flattened pods, expanding in size into a moderate orange yellow (RHS 164B) woody appearance pods when mature.

*Crown distribution*.—Pods can occur throughout the crown, but are most prevalent towards the outer portions of the crown.

*Fruit clusters*.—Pods within a cluster are connected by the rachis of the inflorescence from which they developed, with an average of 5 pods/bunch.

*Pod dimensions*.—Average length of the pod is 33.4 mm, average width of the pod is 18.1 mm, and average thickness of the pod is 8.3 mm. Pods range in shape from oval to half-moon, with an acuminate tip, and average 3.9 g in weight.

Seeds:

*General*.—Typically borne singly in pods. Sometimes an aborted (and much smaller) seed occurs alongside a fully-formed seed. About 1-5% of the pods may have two seeds.

*Seed coat*.—Seeds are covered by a thin seed coat that is usually brownish orange in color (RHS 164A) when matured.

*Seed size*.—Average seed length is 23.0 mm, average seed width is 15.1 mm, and average seed thickness is 6.4 mm. Average seed weight is 2.1 g.

*Seed oil*.—Oil content is 40.6% on a dry-weight basis, which is higher than other similar *Pongamia* cultivars.

*Nut crop*.—Mostly a regular bearer (generally in 2 of 3 years).

*Crop frequency*.—Most *Pongamia* cultivars rarely produce abundant nut crops consistently across multiple years. 'K207' bears pods more regularly than many other cultivars, generally producing a heavier crop in 2 out of 3 years, and a somewhat lighter crop in the third year.

*Ripening*.—Fruit ripening begins in late October and extends into December in southeast Queensland, Australia, and from June-July in Florida, USA. If undisturbed, pods remain in the crown for several weeks after they ripen.

COMPARISON WITH SIMILAR VARIETIES

Unlike *Pongamia* cultivars 'K128b' (U.S. Plant Pat. No. 26,062), 'K140' (U.S. Plant Pat. No. 26,060), and 'K606' (U.S. Plant Pat. No. 26,061), 'K207' has a tendency to produce higher yields of pods in about 2 of 3 years, with pod yields in the third year being somewhat less. This pattern of pod yield tends to resemble the yield pattern of cultivar 'K206' (U.S. Plant patent application Ser. No. 16/602,150), although not necessarily during coincident years.

Seed oil content of 'K207', at 40.6% (dry-weight basis), is higher than 'K206' (38.4%), 'K128b' (38.5%), and 'K606' (38.6%), and is less than that of 'K140' (41.4%).

Inflorescences of 'K207' are compact (short rachis) and generally contain substantial numbers of florets (averaging 80), which is lower than in 'K206', and more than in cultivars 'K128b', 'K140', and 'K606'.

'K207' has semi-pendulous branchlets (similar to 'K128b') compared to strongly pendulous 'K140', which contrasts with the upright branchlets in 'K606' and 'K206'. This semi-pendulous tendency of branchlets gives trees a more closed canopy, which thereby allows less sunlight to reach leaves deeper in the canopy.

'K207' shows unusually large lenticels on the surface of the previous season's branch and other older branches. The branching pattern of the current season's wood of 'K207' shows a greater tendency of axillary buds to develop into a current season's branchlet. The large lenticels and the regular branching pattern are in sharp contrast to 'K206', 'K128b', 'K140', and 'K606'.

Leaves on 'K207' trees include a mix of about ⅔ (two-thirds, or approximately 66%) with 5 leaflets and the remaining ⅓ (one-third, or approximately 33%) with 7 leaflets. This contrasts with cultivars 'K128b', 'K140', and 'K206' in which leaves with 7 leaflets are relatively common.

We claim:

1. A new and distinct variety of *Pongamia pinnata* (L) Pierre tree named 'K207' as illustrated and described herein.

* * * * *